United States Patent
Iwase et al.

(10) Patent No.: US 10,529,045 B2
(45) Date of Patent: *Jan. 7, 2020

(54) INFORMATION PROCESSING APPARATUS AND INFORMATION PROCESSING METHOD

(71) Applicant: CANON KABUSHIKI KAISHA, Tokyo (JP)

(72) Inventors: Yoshihiko Iwase, Kyoto (JP); Akihiro Katayama, Yokohama (JP); Hiroshi Imamura, Kyoto (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/970,157

(22) Filed: May 3, 2018

(65) Prior Publication Data

US 2018/0253812 A1    Sep. 6, 2018

Related U.S. Application Data

(63) Continuation of application No. 12/673,652, filed as application No. PCT/JP2008/065912 on Aug. 28, 2008, now Pat. No. 10,013,727.

(30) Foreign Application Priority Data

Sep. 28, 2007   (JP) ................. 2007-256011

(51) Int. Cl.
   *G06Q 50/22* (2018.01)
   *G06F 19/00* (2018.01)

(52) U.S. Cl.
   CPC ............ *G06Q 50/22* (2013.01); *G06F 19/00* (2013.01)

(58) Field of Classification Search
   USPC ........................................ 382/128
   See application file for complete search history.

(56) References Cited

U.S. PATENT DOCUMENTS 5,519,786 A    5/1996   Courtney et al.
5,526,259 A    6/1996   Kaji
(Continued)

FOREIGN PATENT DOCUMENTS

EP    0616290 A2 *  9/1994    ........... G06F 19/321
JP    03-224055 A   10/1991
(Continued)

OTHER PUBLICATIONS

Japanese Office Action issued in corresponding Japanese Application No. 2007-256011 dated Aug. 17, 2012.
(Continued)

*Primary Examiner* — Amandeep Saini
(74) *Attorney, Agent, or Firm* — Carter, DeLuca & Farrell LLP

(57) ABSTRACT

A report concerning the contents obtained by interpretation based on a medical image can be efficiently created without any constraints of expression. An information processing apparatus according to this invention includes an image analysis unit which acquires information concerning a region name or disease name based on an analysis result on the input medical image, an input unit which inputs the result obtained by interpreting the medical image as character information, a conversion candidate prediction unit which outputs conversion candidates concerning the input character information, and a display control unit which displays the input character information upon converting the character information into character information selected from the conversion candidates. The apparatus further includes a priority level setting unit which sets priority (Continued)

levels in advance for character information output as the conversion candidates.

13 Claims, 18 Drawing Sheets

(56) References Cited

U.S. PATENT DOCUMENTS

| | | |
|---|---|---|
| 5,807,256 A | 9/1998 | Taguchi et al. |
| 6,785,410 B2 | 8/2004 | Vining et al. |
| 7,030,863 B2 | 4/2006 | Longe et al. |
| 7,809,565 B2 | 10/2010 | Coifman |
| 2003/0002748 A1 | 1/2003 | Funahashi |
| 2003/0095147 A1 | 5/2003 | Daw |
| 2004/0236779 A1 | 11/2004 | Kinoshita et al. |
| 2008/0004505 A1 | 1/2008 | Kapit et al. |
| 2012/0253884 A1* | 10/2012 | Koren .................. G06Q 30/02 705/7.29 |
| 2013/0136326 A1 | 5/2013 | Iwase et al. |
| 2017/0236301 A1 | 8/2017 | Kobayashi et al. |
| 2017/0372132 A1 | 12/2017 | Iwase et al. |
| 2018/0137942 A1 | 5/2018 | Sakagawa et al. |

FOREIGN PATENT DOCUMENTS

| | | |
|---|---|---|
| JP | 7-323024 A | 12/1995 |
| JP | 2630405 B2 | 7/1997 |
| JP | 9-293069 A | 11/1997 |
| JP | 2004102509 A | 4/2004 |
| JP | 2004167087 A | 6/2004 |
| JP | 2004-305289 A | 11/2004 |
| JP | 2007-117351 A | 5/2007 |

OTHER PUBLICATIONS

Japanese Office Action issued in corresponding Japanese Application No. 2007-256011 dated May 21, 2012.

* cited by examiner

FIG. 4

| DETECTION IDENTIFIER | TYPE | SELECTION COUNT | CONVERSION CANDIDATE GROUP |
|---|---|---|---|
| | REGION | 5 | INFERIOR PHRENIC LYMPH NODE |
| | REGION | 5 | DESCENDING AORTA |
| | REGION | 12 | LOBUS INFERIOR |
| | REGION | 30 | LOBUS INFERIOR (RIGHT) S6 |
| | REGION | 35 | LOBUS INFERIOR (LEFT) S6 |
| | REGION | 43 | LOBUS INFERIOR (RIGHT) S7 |
| | ⋮ | ⋮ | ⋮ |
| | REGION | 50 | LIVER |
| | REGION | 36 | LIVER ARTERYBRONCHUS |
| | ⋮ | ⋮ | ⋮ |
| | REGION | 5 | BRONCHUS |
| | REGION | 17 | TRACHEOBRONCHIAL LYMPH NODE |
| | REGION | 3 | THORACIC VERTEBRA |
| | REGION | 2 | PLEURA |
| | ⋮ | ⋮ | ⋮ |
| | DISEASE | 50 | NODE |
| | DISEASE | 5 | NODULAR TUBERCULOSIS |
| | DISEASE | 20 | NODULAR HEPATIC CIRRHOSIS |
| | ⋮ | ⋮ | ⋮ |
| | DISEASE | 3 | TUBERCULOSIS |
| | ⋮ | ⋮ | ⋮ |
| | DEGREE | 50 | UNCLEARLY DEMARCATED |
| | DEGREE | 10 | LIGHT |
| | DEGREE | 20 | IRREGULAR |
| | ⋮ | ⋮ | ⋮ |
| | OTHERS | 60 | RECOGNIZE |
| | OTHERS | 50 | CAN SEE |
| | OTHERS | 70 | SUSPECT |

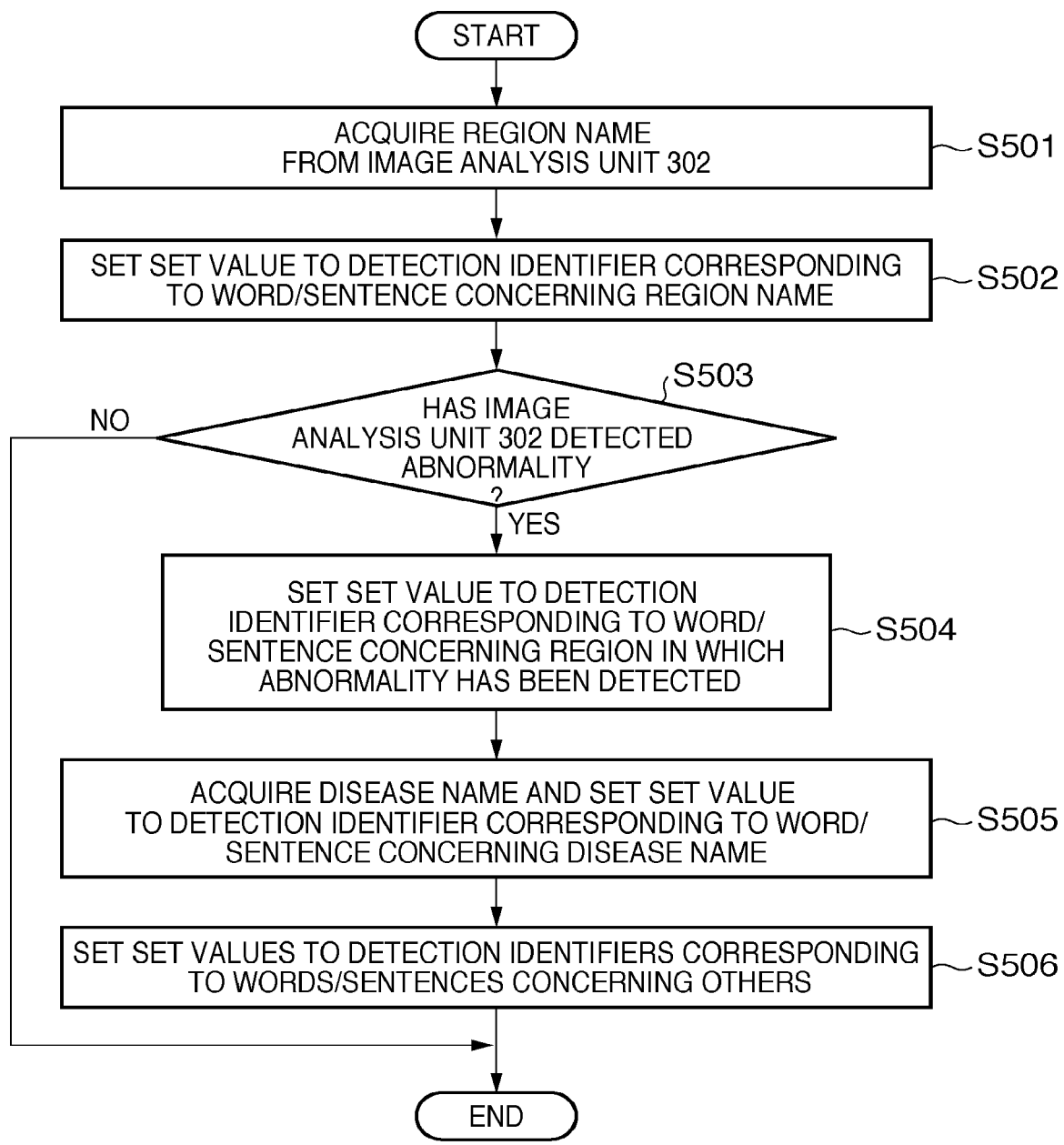

FIG. 6

| | 401 DETECTION IDENTIFIER | 402 TYPE | 403 SELECTION COUNT | 404 CONVERSION CANDIDATE GROUP |
|---|---|---|---|---|
| 601 | 0001 | REGION | 5 | INFERIOR PHRENIC LYMPH NODE |
| 601 | 0001 | REGION | 5 | DESCENDING AORTA |
| 602 | 0011 | REGION | 12 | LOBUS INFERIOR |
| 602 | 0011 | REGION | 30 | LOBUS INFERIOR (RIGHT) S6 |
| 601 | 0001 | REGION | 35 | LOBUS INFERIOR (LEFT) S6 |
| 601 | 0001 | REGION | 43 | LOBUS INFERIOR (RIGHT) S7 |
| | : | : | : | : |
| 601' | 0000 | REGION | 50 | LIVER |
| 601' | 0000 | REGION | 36 | LIVER ARTERYBRONCHUS |
| | : | : | : | : |
| 601 | 0001 | REGION | 5 | BRONCHUS |
| 601 | 0001 | REGION | 17 | TRACHEOBRONCHIAL LYMPH NODE |
| 601 | 0001 | REGION | 3 | THORACIC VERTEBRA |
| 601 | 0001 | REGION | 2 | PLEURA |
| | : | : | : | : |
| 604 | 0001 | DISEASE | 50 | NODE |
| 604 | 0001 | DISEASE | 5 | NODULAR TUBERCULOSIS |
| 603 | 0000 | DISEASE | 20 | NODULAR HEPATIC CIRRHOSIS |
| | : | : | : | : |
| 604 | 0001 | DISEASE | 3 | TUBERCULOSIS |
| | : | : | : | : |
| 605 | 0011 | DEGREE | 50 | UNCLEARLY DEMARCATED |
| 605 | 0011 | DEGREE | 10 | LIGHT |
| 605 | 0011 | DEGREE | 20 | IRREGULAR |
| | : | : | : | : |
| 606 | 0011 | OTHERS | 60 | RECOGNIZE |
| 606 | 0011 | OTHERS | 50 | CAN SEE |
| 606 | 0011 | OTHERS | 70 | SUSPECT |

FIG. 12

| | DETECTION IDENTIFIER (401) | TYPE (402) | SELECTION COUNT (403) | CONVERSION CANDIDATE GROUP (404) |
|---|---|---|---|---|
| 1202 | 0001 | REGION | 5 | INFERIOR PHRENIC LYMPH NODE |
| 1202 | 0001 | REGION | 5 | DESCENDING AORTA |
| 1204 | 0011 | REGION | 12 | LOBUS INFERIOR |
| 1204 | 0011 | REGION | 30 | LOBUS INFERIOR (RIGHT) S6 |
| 1202 | 0001 | REGION | 35 | LOBUS INFERIOR (LEFT) S6 |
| 1202 | 0001 | REGION | 43 | LOBUS INFERIOR (RIGHT) S7 |
| | : | : | : | : |
| 1203 | 0111 | REGION | 50 | LIVER |
| 1201 | 0101 | REGION | 26 | LIVER ARTERYBRONCHUS |
| | : | : | : | : |
| | 0001 | REGION | 5 | BRONCHUS |
| | 0001 | REGION | 17 | TRACHEOBRONCHIAL LYMPH NODE |
| 1202 | 0001 | REGION | 3 | THORACIC VERTEBRA |
| | 0001 | REGION | 2 | PLEURA |
| | : | : | : | : |
| 1205 | 0001 | DISEASE | 50 | NODE |
| 1208 | 0111 | DISEASE | 5 | NODULAR TUBERCULOSIS |
| 1206 | 0101 | DISEASE | 20 | NODULAR HEPATIC CIRRHOSIS |
| | : | : | : | : |
| 1207 | 0001 | DISEASE | 3 | TUBERCULOSIS |
| | : | : | : | : |
| 1209 | 0011 | DEGREE | 50 | UNCLEARLY DEMARCATED |
| | | DEGREE | 10 | LIGHT |
| | | DEGREE | 20 | IRREGULAR |
| | : | : | : | : |
| 1209 | 0011 | OTHERS | 60 | RECOGNIZE |
| | 0011 | OTHERS | 50 | CAN SEE |
| | 0011 | OTHERS | 70 | SUSPECT |

FIG. 18

| 1801 | 1802 | 1803 |
|---|---|---|
| REGION LIST | DISEASE LIST | MODIFIER LIST |
| LOBUS INFERIOR (RIGHT) S6 | NODE | UNCLEARLY DEMARCATED |
| LUNG | TUMOR | LIGHT |
| LIVER | FROSTED-GLASS-LIKE SHADOW | : |
| : | : | : |

INFORMATION PROCESSING APPARATUS AND INFORMATION PROCESSING METHOD

CROSS REFERENCE TO RELATED APPLICATIONS

This application is a continuation of U.S. patent application Ser. No. 12/673,652 filed on Feb. 16, 2010, which is a National Stage Application of PCT International Application No. PCT/JP2008/065912 filed on Aug. 28, 2008, which claims the benefit of and priority to Japanese Patent Application No. 2007-256011 filed on Sep. 28, 2007, the entire contents of each of which are hereby incorporated by reference herein in its entirety.

TECHNICAL FIELD

The present invention relates to an information processing technique in an information processing apparatus for creating a report concerning an interpretation result on a medical image.

BACKGROUND ART

In the medical field, the digitization of the medical images obtained by imaging objects has been implemented. This makes it possible to monitor-display the medical image data output from medical imaging apparatuses such as a CR apparatus, a CT apparatus, an MRI apparatus, and an ultrasonic apparatus at the time of diagnosis. A doctor then makes diagnosis by interpreting such monitor-displayed medical images and observing the state of a morbid region and its temporal change. Note that CR, CT, and MRI respectively stand for Computed Radiography, Computed Tomography, and Magnetic Resonance Imaging.

Conventionally, a medical image processing apparatus called a computer-aided diagnosis apparatus which can automatically detect a morbid region as an abnormal shadow candidate by image analysis on medical image data has been developed to reduce the load on a doctor making diagnosis.

This medical image processing apparatus can detect abnormal shadow candidates such as an abnormal tumor shadow indicating a cancer or the like and a high-density micro calcification shadow based on input medical image data. Automating part of diagnosing operation by the doctor in this manner can reduce the load on the doctor making diagnosis and improve the accuracy of a diagnosis result.

In making diagnosis based on medical images, the doctor needs to create a report concerning an interpretation result as a diagnosis result in addition to interpreting a medical image. The operation of creating this report also imposes a very heavy load on the doctor.

On the other hand, a medical image processing apparatus which allows to create a report concerning an interpretation result by only selecting a form text which is created in advance when interpretation results are input has been proposed to reduce the load of the operation of creating such reports (see, for example, Japanese Patent Laid-Open No. 2004-167087).

In the case of Japanese Patent Laid-Open No. 2004-167087, however, since a report is created by filling in blanks concerning the respective items with selected character strings in the mode defined by a form text, expressions about an interpretation result are limited.

It is also effective to use a so-called input prediction technique of displaying words/sentences, as conversion candidates, concerning a character which is being input instead of a form text. The conventional input prediction technique is designed to display words with high input frequencies and recently input words at higher ranks in conversion candidates. That is, this technique is not designed to preferentially display words/sentences suitable for interpreted medical images. Even if, therefore, the input prediction technique is used, it is not necessarily possible to efficiently create a report.

DISCLOSURE OF INVENTION

The present invention has been made in consideration of the above problems, and has as its object to allow to efficiently create a report concerning an interpretation result on a medical image without any constraints of expression. In addition, other objects and features of the present invention will be apparent from the following specification and the drawings.

In order to achieve the above objects, an information processing apparatus according to the present invention has the following arrangement.

This apparatus is characterized by comprising: image input means for inputting a medical image obtained by imaging an object by using a medical imaging apparatus; and output means for outputting a plurality of pieces of character information as candidates of character information forming a document representing a result obtained by interpreting the input medical image on the basis of an analysis result on the input medical image.

According to the present invention, it is possible to efficiently create a report concerning an interpretation result on a medical image without any constraints of expression.

Further features of the present invention will become apparent from the following description of exemplary embodiments with reference to the attached drawings.

BRIEF DESCRIPTION OF DRAWINGS

The accompanying drawings, which are incorporated in and constitute a part of the specification, illustrate embodiments of the invention and, together with the description, serve to explain the principles of the invention.

FIG. 4 is a view showing an example of the arrangement of a conversion candidate table;

FIG. 5 is a flowchart showing the contents of processing in a priority level setting unit;

FIG. 6 is a view showing an example of a conversion candidate table in which detection identifiers are set;

FIG. 12 is a view showing an example of a conversion candidate table in which detection identifiers are set;

FIG. 18 is a view showing an example of display of conversion candidates in the medical image processing apparatus.

BEST MODE FOR CARRYING OUT THE INVENTION

The best mode for carrying out the present invention will be described below with reference to the accompanying drawings. Note that a medical image processing apparatus as an information processing apparatus according to each embodiment to be described below displays, as conversion candidates, words/sentences concerning a character input by a doctor in inputting an interpretation result on a medical image. In this case, the medical image processing apparatus is characterized by displaying conversion candidates on the basis of the priority levels set based on an analysis result on the medical image.

In the following description of each embodiment, assume that "words/sentences concerning an input (recognized) character" are words/sentences starting from the input character. Words/sentences starting from an input character are extracted from a plurality of words/sentences registered in advance in a conversion candidate table functioning as a dictionary and are displayed as "conversion candidates".

In addition, "words/sentences concerning a region name or disease name" include a word straightly expressing the region name or disease name, a word expressing a superordinate concept of the region name or disease name, and a sentence including the region name or disease name. Assume also that such words/sentences include words/sentences which are customarily used when sentences are created by using the region name or disease name.

First Embodiment

<1. Arrangement of Medical Image Processing System>

Figure 1:
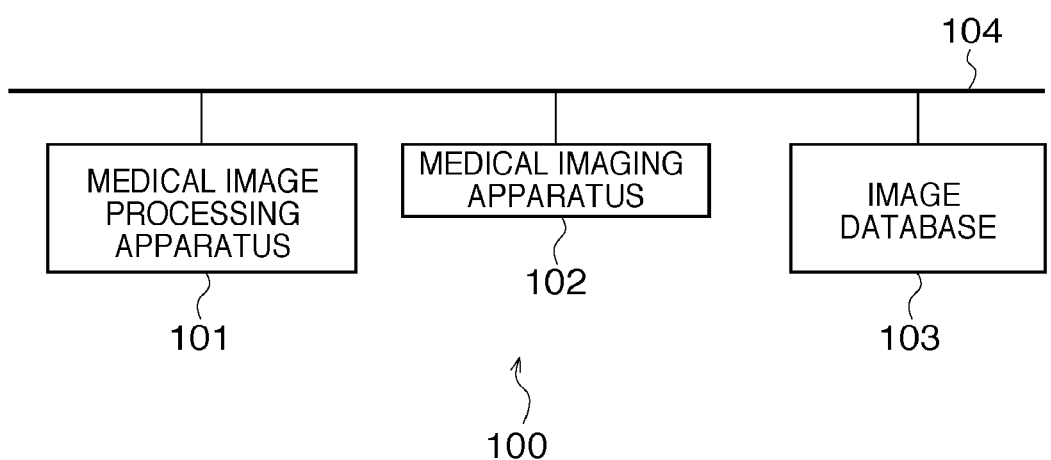
FIG. 1 is a block diagram showing the arrangement of a medical image processing system including a medical image processing apparatus as an information processing apparatus according to the first embodiment of the present invention.

FIG. 1 is a block diagram showing the arrangement of a medical image processing system 100 including a medical image processing apparatus as an information processing apparatus according to the first embodiment of the present invention.

As shown in FIG. 1, the medical image processing system comprises a medical image processing apparatus 101, a medical imaging apparatus 102, and an image database 103, which are communicatively connected to each other via a network 104.

The medical imaging apparatus 102 is an apparatus which generates medical images by imaging an object, and includes an X-ray device, CT, MRI, PET, ultrasonic diagnosis apparatus, OCT, and the like. Note that PET stands for Positron Emission Tomography, and OCT stands for Optical Coherence Tomography.

The image database 103 stores each medical image captured by the medical imaging apparatus 102 upon addition of management attribute information such as an examination date, hospital name, patient name, birth date, examination type, and examination region.

The medical image processing apparatus 101 is an apparatus for displaying a medical image captured by the medical imaging apparatus 102 or a medical image stored in the image database 103, inputting, as character information, an interpretation result obtained by a doctor based on the displayed medical image, and creating a report.

<2. Hardware Arrangement of Medical Image Processing Apparatus 101>

Figure 2:
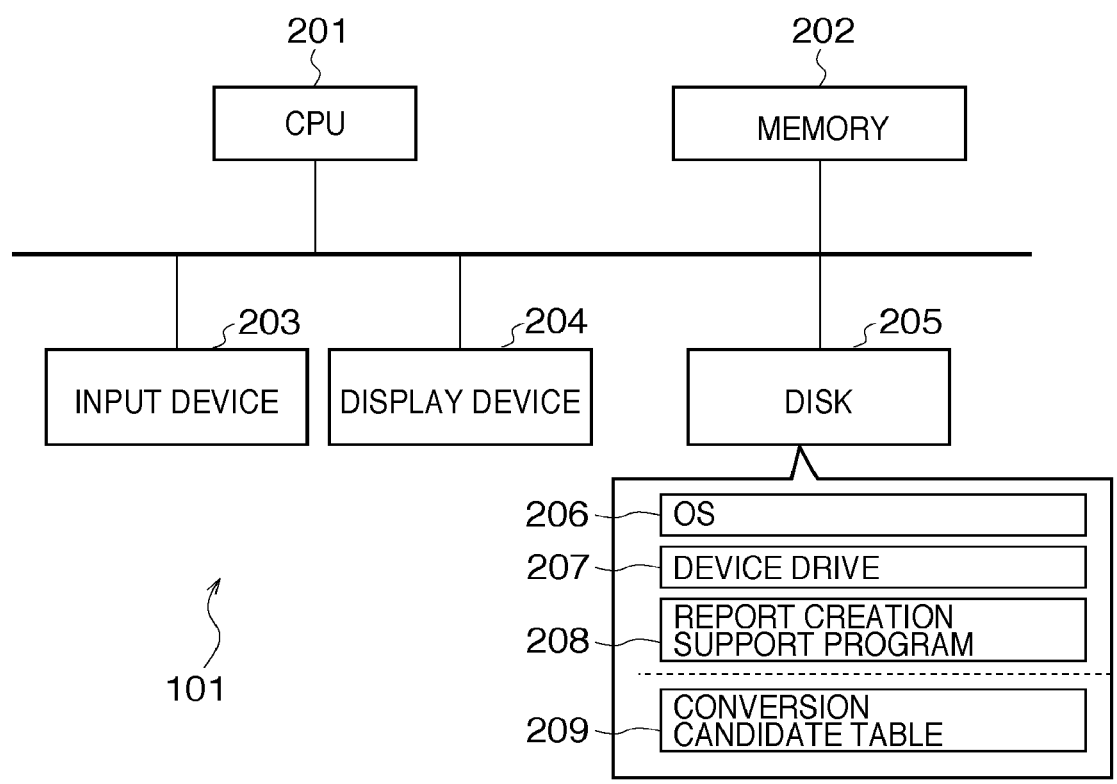
FIG. 2 is a block diagram showing the hardware arrangement of the medical image processing apparatus.

FIG. 2 is a block diagram showing the hardware arrangement of the medical image processing apparatus 101. As shown in FIG. 2, the medical image processing apparatus 101 comprises a CPU (Central Processing Unit) 201, an input device 203, a display device 204, a memory 202, a disk 205 as constituent elements.

The CPU 201 executes various control programs and controls the operation of each constituent element of the medical image processing apparatus 101. The input device 203 accepts a pointing input and an input of a character or the like by the doctor. The display device 204 displays an execution result on each type of control program which is obtained by the CPU 201. The display device 204 includes, for example, a CRT monitor and a liquid crystal monitor.

The memory 202 stores predetermined control programs, and provides a work area at the time of execution of a control program. The disk 205 stores various kinds of control programs including an operating system (OS) 206, a device drive 207 for peripheral devices, and a control program (to be referred to as a report creation support program 208) for implementing an image processing method according to the present invention. The disk further stores data and the like used in the execution of various types of control programs (e.g., a conversion candidate table 209 (to be described in detail later) used when the report creation support program 208 is executed).

<3. Functional Arrangement of Medical Image Processing Apparatus 101>

Each function implemented by executing the report creation support program 208 of the medical image processing apparatus 101 (to be simply referred to as each function which the medical image processing apparatus 101 has hereinafter) will be described next.

Figure 3:
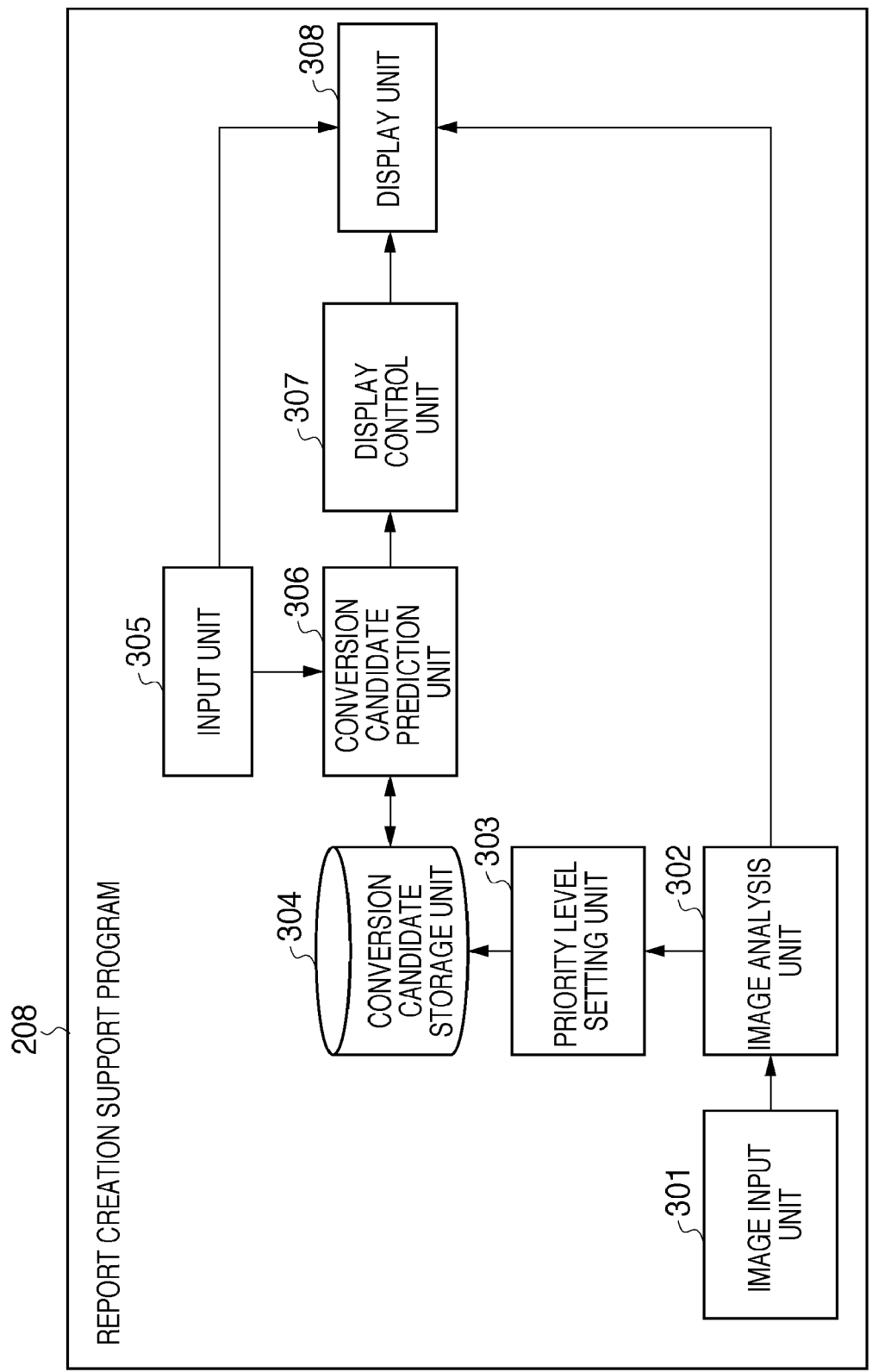
FIG. 3 is a block diagram showing the arrangement of the respective functions implemented when a report creation support program is executed.

FIG. 3 is a block diagram showing the arrangement of the respective functions which the medical image processing apparatus 101 has. As shown in FIG. 3, each function which the medical image processing apparatus 101 has includes an image input unit 301 which inputs the medical image data transmitted from the medical imaging apparatus 102 or the image database 103.

The above functions also include an image analysis unit 302 which performs image analysis on input medical image data and specifies a region name, a disease name, or the like (information concerning diagnosis of an object) which can be used for input operation of an interpretation result. The functions further include a priority level setting unit 303 which sets priority levels used for display operation of conversion candidates extracted from the words/sentences registered in the conversion candidate table 209 on the basis of the image analysis result obtained by the image analysis unit 302.

The above functions further include a conversion candidate storage unit 304 which stores the conversion candidate table 209, in which a plurality of words/sentences are registered, in the disk 205 to provide words/sentences concerning the character input via the input device 203 and recognized by an input unit 305.

The above functions also include the input unit 305 which recognizes the character input via the input device 203, and a conversion candidate prediction unit 306 which extracts words/sentences concerning the character recognized by the input unit 305 from the conversion candidate table 209 as conversion candidates. Note that the conversion candidate prediction unit 306 can also discriminate one of the extracted conversion candidates which is actually selected by the doctor and set the number of times of selection of the selected conversion candidate in the conversion candidate table 209.

In addition, the above functions include a display control unit 307 which performs control to display the conversion candidates extracted by the conversion candidate prediction unit 306 in accordance with the priority levels set in correspondence with the conversion candidates.

Furthermore, the above functions include a display unit 308 which displays the character recognized by the input unit 305, displays the conversion candidates extracted by the conversion candidate prediction unit 306 under the control of the display control unit 307, and displays the medical image data input by the image input unit 301.

<4. Arrangement of Conversion Candidate Table>

FIG. 4 is a view showing an example of the arrangement of the conversion candidate table 209. As shown in FIG. 4, in the conversion candidate table 209, a plurality of words/sentences are registered in "conversion candidate group" 404 so as to provide words/sentences concerning the character recognized by the input unit 305 as conversion candidates.

In "type" 402, information is registered, which indicates whether each word/sentence registered in "conversion candidate group" 404 is a word/sentence concerning a region name of the human body, a word/sentence concerning a disease name, a word/sentence concerning the degree of a disease, or another word/sentence. Assume that "conversion candidate group" 404 and "type" 402 are registered in the conversion candidate table 209 before the execution of the report creation support program 208.

The conversion candidate table 209 is configured to set "detection identifier" 401 and "selection count" 403 in correspondence with each word/sentence registered in "conversion candidate group" 404.

"Detection identifier" 401 is an identifier indicating a priority level which is used when each word/sentence registered in "conversion candidate group" 404 is displayed as a conversion candidate, and is set by the priority level setting unit 303 (this operation will be described in detail later).

In addition, "selection count" 403 is the number of times of use of a conversion candidate of the conversion candidates extracted by the conversion candidate prediction unit 306 which has been actually selected by the doctor and used in report creation, and is set by the conversion candidate prediction unit 306.

The set values set in "detection identifier" 401 will be described next. The set values which are set in "detection identifier" 401 in correspondence with the words/sentences corresponding to "region" registered in "type" 402 will be described here as an example.

"0000" is set in "detection identifier" 401 associated with a word/sentence, of the words/sentences registered in "conversion candidate group" 404 of the conversion candidate table 209, which concerns the region name of a region which is not included in the input medical image data.

"0001" is set in "detection identifier" 401 associated with a word/sentence, of the words/sentences registered in "conversion candidate group" 404 of the conversion candidate table 209, which concerns the region name of a region which is included in the input medical image data.

"0011" is set in "detection identifier" 401 associated with a word/sentence which is included in the input medical image data and concerns the region name of a region in which abnormality has been detected.

If it is determined during creation of a report that a description about a specific region name or disease name is complete, "0010" is re-set in "detection identifier" associated with a word/sentence concerning the specific region name or disease name.

Assume that the priority levels of the values set in "detection identifier" 401 in this manner are 0011>0001>0010>0000 in the display control unit 307.

In this manner, when extracting and displaying conversion candidates from the conversion candidate table for the character input by the doctor, the medical image processing apparatus according to this embodiment sets, in advance, priority levels based on analysis results on medical images for the words/sentences registered in the conversion candidate table.

With this operation, conversion candidates suitable for a medical image are preferentially displayed, and the doctor can efficiently create a report.

Note that the number of bits of each set value set in "detection identifier" 401 of the conversion candidate table 209 is not specifically limited, and may be larger or smaller than four bits. In addition, the types of set values are not limited to the four types, that is, 0011, 0001, 0010, and 0000.

<5. Function of Image Analysis Unit 302>

The contents of processing in the image analysis unit 302 will be described next. The image analysis unit 302 performs image analysis on the medical image data input by the image input unit 301, and detects a region included in the medical image data.

More specifically, if input medical image data is chest CT image data, this unit segments the medical image data into regions, for example, a lung field, diaphragm, bronchus, pulmonary artery, and pulmonary vein, and further segments the lung field into regions, for example, a lobus superior, lobus medius, and lobus inferior. Note, however, that the types of regions into which image data is segmented are not limited to them.

Assume that this embodiment uses the level set method as a kind of dynamic contour method to detect a region included in medical image data. According to the level set method, a level set function higher than the dimension of a detection target region by one dimension is defined, and the region to be detected is regarded as a zero contour of the function. This function is then updated based on the following evolution equation called a level set equation to control the contour and detect the region.

$$\varphi t + F|\nabla\varphi| = 0$$

where φt is the value obtained by calculating the first derivative of the level set function in the time axis direction, F is the growth speed of the contour, and |∇φ| is the absolute value of the gradient of the level set function.

The above description has exemplified the method of detecting a region by using the level set method. Other than this method, however, the region detection method can be, for example, a method based on threshold processing, region growing method, dynamic contour method, clustering method, or minimum graph cut method. It suffices to detect a region by using one of these techniques or another technique. Alternatively, these detection methods can be selectively used in accordance with regions. In addition, it suffices to detect a region by using a probability atlas, a human figure model, or the like as pre-knowledge as well as using image feature amounts.

The image analysis unit 302 further specifies the region name of the detected region by collating with medical knowledge. If, for example, the medical image data is medical image data about a chest portion, region names such as a pulmonary lung, segment, bronchus, lymph gland, and artery/vein are specified.

The image analysis unit 302 further detects an abnormality such as lung cancer from the region in addition to specifying the above region name.

A method of detecting an abnormality can be, for example, filter processing for detecting an abnormality, pattern matching processing, abnormality detection processing using a discriminator, or the processing of detecting the difference between a past image, an average shape image, or the like and a medical image as a target by registration. The image analysis unit 302 detects an abnormality by using one of these techniques or another technique.

In addition, the image analysis unit 302 performs disease classification and benignity/malignity discrimination for a detected abnormality. Assume that a discriminator such as a support vector machine, AdaBoost, Bayesian discriminator, or neuralnet is used for disease classification and benignity/malignity discrimination for a detected abnormality. Note that the discriminator to be used is not limited to them.

<6. Function of Priority Level Setting Unit 303>

The contents of processing in the priority level setting unit 303 will be described next with reference to FIG. 6 using the flowchart of FIG. 5.

In step S501, the CPU 201 acquires the region names specified by the image analysis unit 302.

In step S502, the CPU 201 searches the conversion candidate table 209 to discriminate words/sentences concerning each region name acquired in step S501 (words/sentences corresponding to "region" in "type" 402). The CPU 201 sets "0001" in "detection identifier" 401 associated with the discriminated word/sentence.

Assume that the medical image data includes regions such as an inferior phrenic lymph node, descending aorta, lobus inferior S7, bronchus, tracheobronchial lymph node, thoracic vertebra, and pleura. As shown in FIG. 6, therefore, "0001" is set in "detection identifier" 401 associated with words/sentences concerning these region names in the conversion candidate table 209 (see "601"). Note that a liver and a liver artery are regions which are not included in the medical image data. For this reason, in the case shown in FIG. 6, "0000" remains the same in "detection identifier" 401 associated with words/sentences concerning these region names (see "601'").

In step S503, the CPU 201 causes a branch depending on whether the image analysis unit 302 has detected an abnormality. If the image analysis unit 302 has detected no abnormality, the CPU 201 terminates the processing in the priority level setting unit 303.

If the image analysis unit 302 has detected an abnormality, the process advances to step S504. In step S504, the CPU 201 sets "0011" in "detection identifier" 401 associated with a word/sentence concerning the region name of the region in which the abnormality has been detected (a word/sentence corresponding to "region" in "type" 402) to increase the priority level of the word/sentence.

Assume that an abnormality has been detected in a lobus inferior (right) S6 of the regions included in the medical image data. As a consequence, as shown in FIG. 6, "0011" is set in "detection identifier" 401 associated with the lobus inferior (right) S6 and lobus inferiors including the lobus inferior (right) S6 (see "602").

In step S505, the CPU 201 acquires the disease name detected by the image analysis unit 302, and searches the conversion candidate table 209 based on the disease name. If there is any word/sentence concerning the disease name (the word/sentence corresponding to "disease" in "type" 402), the CPU 201 sets a predetermined set value in "detection identifier" 401 associated with the word/sentence.

More specifically, the CPU 201 sets "0001" in "detection identifier" 401 associated with the word/sentence concerning the acquired disease name (the word/sentence corresponding to "disease" in "type" 402).

Note that the CPU 201 sets "0000" in "detection identifier" 401 associated with a word/sentence concerning the acquired disease name (a word/sentence corresponding to "disease" in "type" 402) if the word/sentence concerns the disease which can develop only in an organ area other than the organ area in which the disease has developed.

The CPU 201 also sets "0000" in "detection identifier" 401 associated with a word/sentence (a word/sentence corresponding to "disease" in "type" 402) other than those concerning the acquired disease name.

Assume that the organ area is a chest portion, and the disease name acquired in step S505 is a nodular hepatic cirrhosis. In this case, as shown in FIG. 6, "0000" is kept set in "detection identifier" 401 corresponding to a word concerning a disease name (e.g., a nodular hepatic cirrhosis) which can develop only in an abdominal portion or head portion (see "603").

On the other hand, "0001" is set in "detection identifier" 401 corresponding to a word/sentence concerning the acquired disease name (e.g., a nodular tuberculosis or tuberculosis) (see "604").

In step S506, the CPU 201 sets "0011" in "detection identifier" 401 corresponding to another word/sentence (a word/sentence corresponding to "degree" in "type" 402) concerning the region name acquired in step S501 and the disease name acquired in step S505.

If, for example, an unclearly demarcated node is detected in the lobus inferior (right) S6, the CPU 201 sets "0011" in "detection identifier" 401 corresponding to words like "unclearly demarcated", "light", and "irregular" as words/sentences indicating the degree of the disease (see "605").

In addition, the CPU 201 sets "0011" in "detection identifier" 401 associated with words/sentences like "recognize" and "can see" (words/sentences corresponding to "others" in "type" 402) which concern the acquired region name or disease name (see "606").

<7. Function of Conversion Candidate Prediction Unit 306>

The contents of processing in the conversion candidate prediction unit 306 will be described next. In the conversion candidate prediction unit 306, the CPU 201 searches the conversion candidate table 209 stored in the conversion candidate storage unit 304 and reads out conversion candidates concerning the character recognized by the input unit 305.

A method of reading out conversion candidates will be described below with reference to FIGS. 7A and 7B.

Figure 7A:
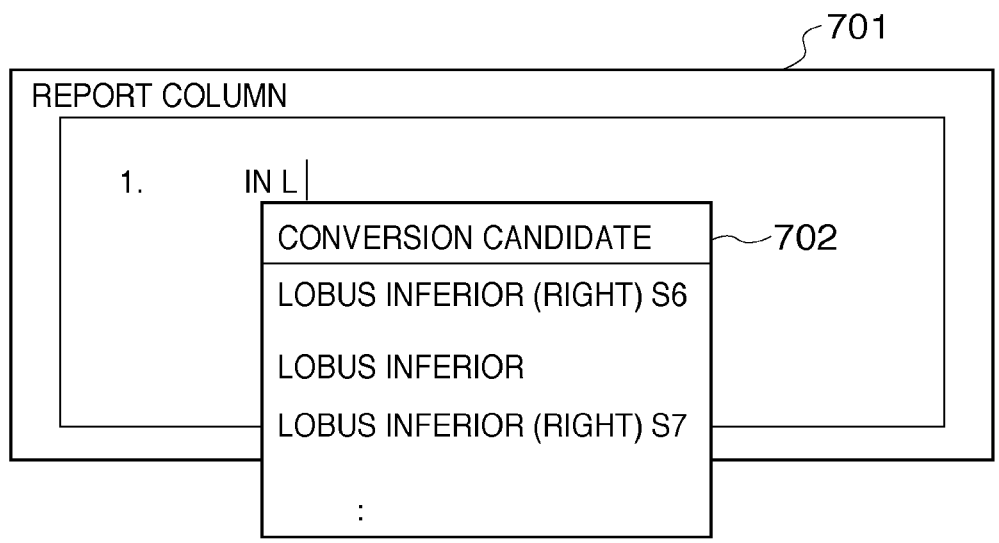
FIGS. 7A and 7B are views each showing an example of a UI for report creation in the medical image processing apparatus.
Figure 7B:
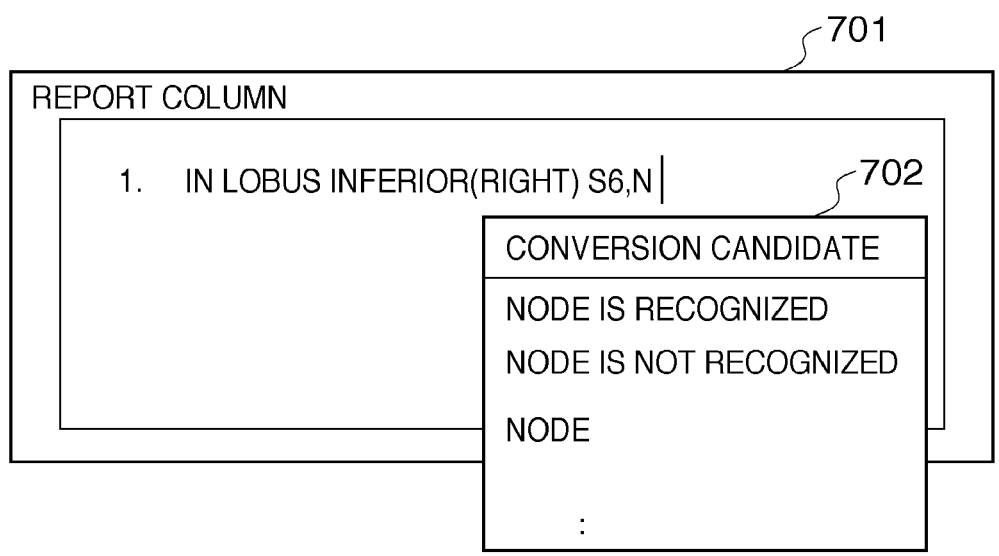

FIGS. 7A and 7B are views each showing an example of a UI for report creation in the medical image processing apparatus 101. Assume that the doctor has input the character "1" in a report column 701 displayed on the display device 204 of the medical image processing apparatus 101.

In this case, if conversion candidates of the character (words/sentences starting from "1") are read out from the conversion candidate table 209 in descending order of selection counts as in the prior art, liver, lobus inferior (right) S7, liver artery, lobus inferior (left) S6, lobus inferior (right) S6, and the like are read out in the order named.

In contrast to this, the conversion candidate prediction unit 306 reads out and arranges conversion candidates based on the priority levels of the set values set in "detection identifier" 401 and "selection count" 403 instead of reading out conversion candidates based on the selection counts and the order in which they have currently been read out.

In this case, since the priority levels of the set values set in "detection identifier" are 0011>0001>0010>0000, lobus inferior (right) S6, lobus inferior, lobus inferior (right) S7, lobus inferior (left) S6, . . . , liver, liver artery, . . . are read out in the order named in the example of FIG. 7A. The display unit 308 displays the conversion candidates read out from the conversion candidate table 209 by the display control unit 307.

Note that a method of displaying readout conversion candidates can be a method of displaying the conversion candidates in a pull-down menu form or pop-up form near the cursor of the input character as indicated by "702" in FIGS. 7A and 7B, or a method of displaying the conversion candidates in another window.

Assume also that the display position of conversion candidates can be set to an upper, lower, right, or left position on the window, and the doctor can arbitrarily set a display size. Assume that the number of conversion candidates to be displayed can be arbitrarily set. Furthermore, conversion candidates can be displayed in a sentence form instead of on a word basis, as shown in FIG. 7B.

Upon detecting at least one of the region names or disease names written in the report column 701 by the doctor, the conversion candidate prediction unit 306 determines that an interpretation result concerning the detected region name or disease name has already been written (converted) as a report.

Note that a method of determining whether an interpretation result has been written can be a method of determining that an interpretation result has been written when the corresponding region name or disease name has been used once, or a method of determining that an interpretation result has been written upon detecting a paragraph or punctuation mark. Alternatively, it suffices to use a method of determining that an interpretation result has been written upon recognizing the meaning of a sentence by syntactic analysis/semantic analysis.

Upon determining that the interpretation result has been written, the conversion candidate prediction unit 306 sets "0010" in "detection identifier" 401 associated with a word/sentence concerning the written region name or disease name which is registered in the conversion candidate table 209.

Figure 8:
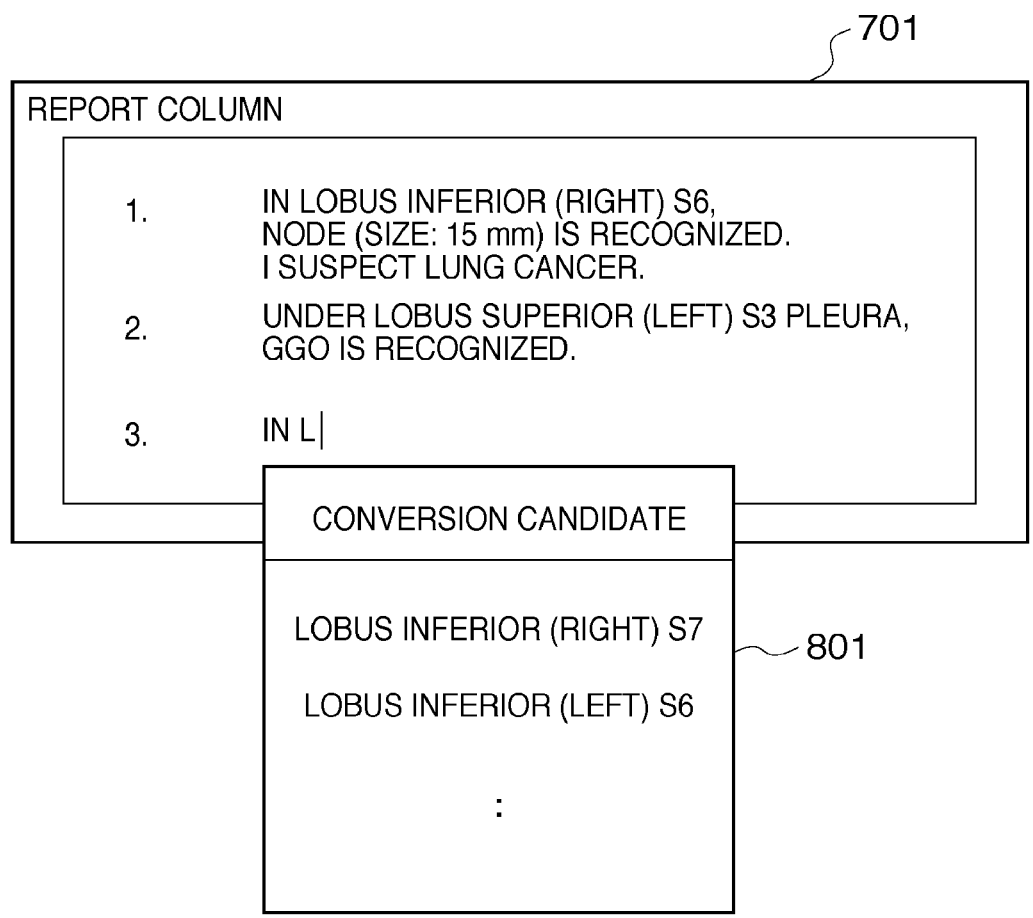
FIG. 8 is a view showing an example of a UI for report creation in the medical image processing apparatus.

This decreases the priority level of the word/sentence concerning the region name or disease name which has already been written in the report as the interpretation result. As a consequence, as shown in FIG. 8, a word/sentence concerning a region name or disease name which has not been written in the report column 701 is displayed at a higher position in a pull-down menu 801.

Note that the conversion candidate prediction unit 306 may be configured to extract words/sentences concerning the character recognized by the input unit 305 upon narrowing down them in accordance with an examination purpose, for example, screening, detailed examination, or follow-up, instead of extracting all the words/sentences.

In this case, it suffices to separately form conversion candidate tables corresponding to examination purposes and extract conversion candidates by searching the conversion candidate tables.

Alternatively, it suffices to form a common conversion candidate table, set in advance specific set values to detection identifiers associated with words/sentences matching examination purposes, and extract only conversion candidates corresponding to detection identifiers to which specific set values are set. Note that words/sentences matching examination purposes are, for example, words/sentences expressing an increase/decrease in the number of nodes or a change in the size of nodes, which indicate the stage of development of a disease (words/sentences corresponding to "others" in "type" 402).

As is obvious from the above description, the medical image processing apparatus according to this embodiment is configured to display conversion candidates on the basis of the priority levels set in accordance with an analysis result on a medical image when displaying words/sentences concerning an input character as conversion candidates.

This makes it possible to display conversion candidates which are likely to be selected. The doctor can therefore efficiently create a report concerning an interpretation result on the basis of a medical image without any constraints of expression.

Second Embodiment

The first embodiment has exemplified the case in which one medical image data is input by the image input unit. However, the medical image processing apparatus according to the present invention is not limited to the case in which one medical image data is input, and can be applied to a case in which a plurality of medical image data are simultaneously input. The case in which a plurality of medical image data is simultaneously input includes, for example, a case in which consecutive medical image data at different slice positions in the same organ area are input.

As described above, when a plurality of medical image data are simultaneously input, different region names or disease names may be detected from the respective medical image data as a result of image analysis.

For this reason, this embodiment is configured to manage which medical image the doctor currently interprets and to increase (preferentially display) the priority level of a word/sentence concerning a region name or disease name detected from the medical image which the doctor currently interprets. The embodiment is further configured to manage medical images which the doctor has already interpreted and decrease (non-preferentially display) the priority level of a word/sentence concerning a region name or disease name detected from a medical image which the doctor has already interpreted.

The medical image processing apparatus according to this embodiment will be described in detail below.

<1. Functional Arrangement of Medical Image Processing Apparatus>

Figure 9:
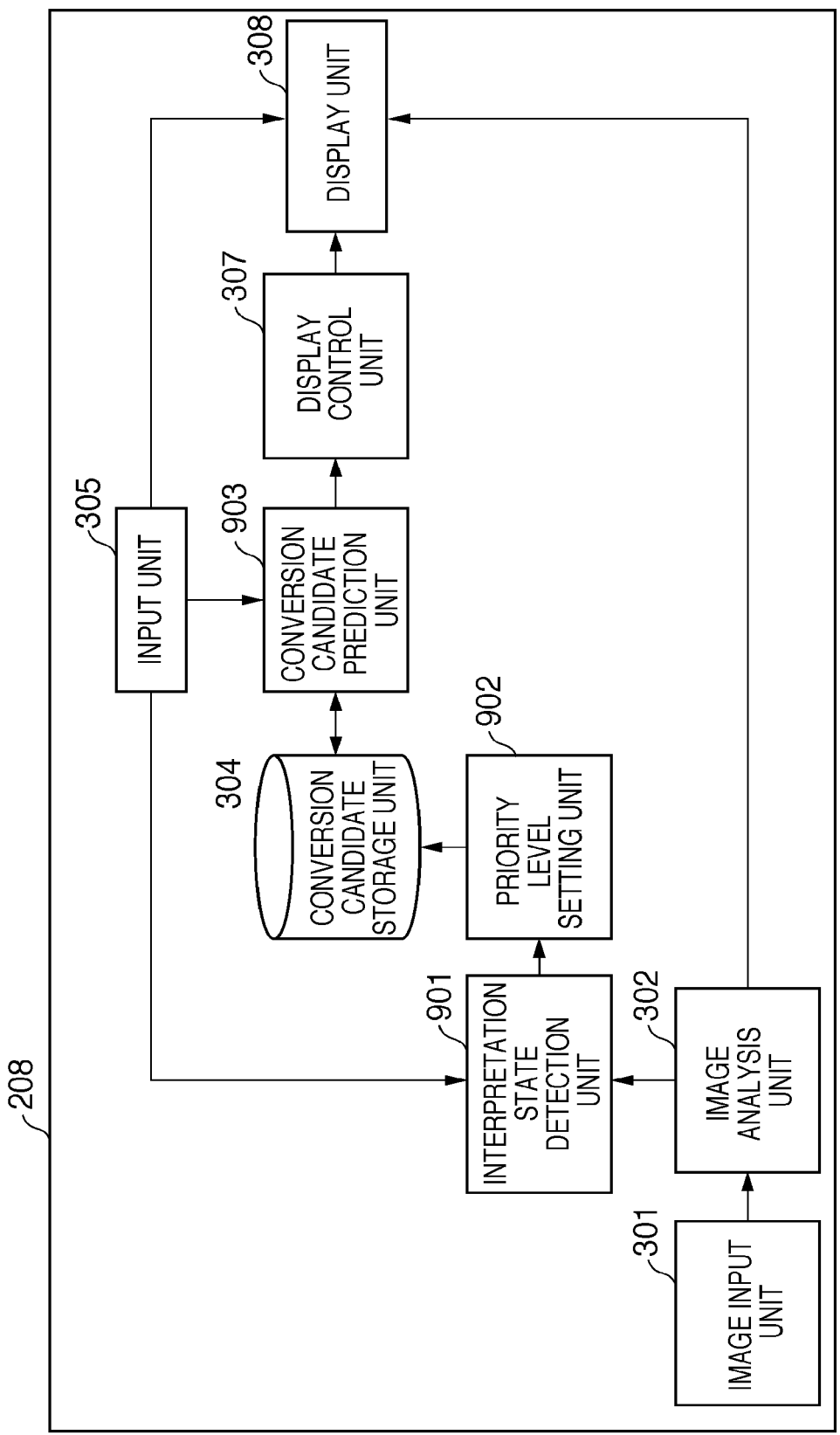
FIG. 9 is a block diagram showing the functional arrangement of a medical image processing apparatus as an information processing apparatus according to the second embodiment of the present invention.

FIG. 9 is a block diagram showing the functional arrangement of the medical image processing apparatus as an information processing apparatus according to the second embodiment of the present invention. The functional arrangement of the medical image processing apparatus according to this embodiment is basically the same as that of the medical image processing apparatus according to the first embodiment. Note, however, the functions implemented in the medical image processing apparatus according to this embodiment further include an interpretation state detection unit 901 which detects the interpretation state of a doctor.

<2. Function of Interpretation State Detection Unit>

Figure 10:
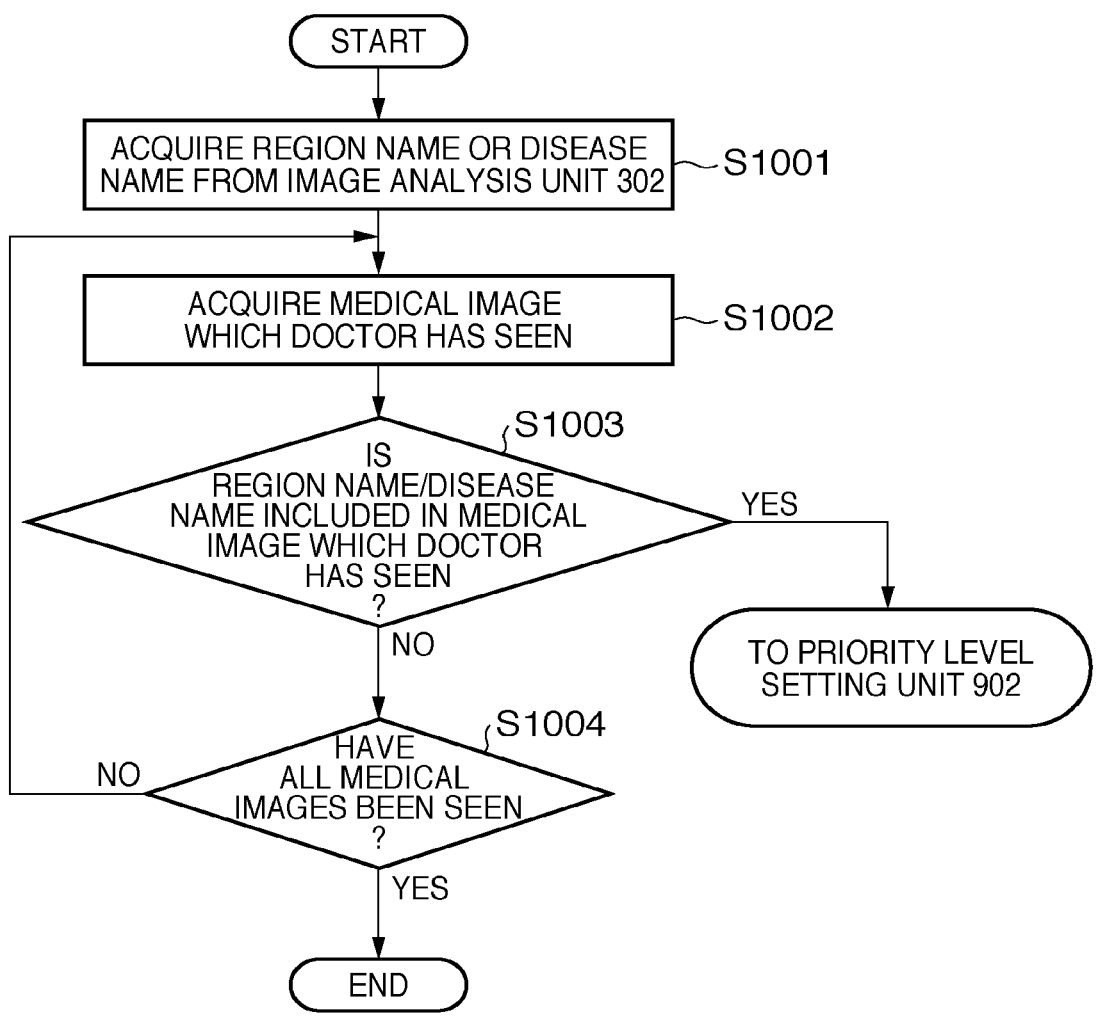
FIG. 10 is a flowchart showing the contents of processing in an interpretation state detection unit.

The contents of processing in the interpretation state detection unit 901 will be described with reference to the flowchart of FIG. 10. In step S1001, a CPU 201 acquires all the region names or disease names specified by an image analysis unit 302. With this operation, all the region names/disease names included in a plurality of input medical image data are acquired.

In step S1002, the CPU 201 acquires the interpretation state of the doctor (the medical images which the doctor has interpreted). More specifically, if a plurality of slice images of CT data is input as medical images, the CPU 201 acquires a slice No. history as medical images which the doctor has interpreted.

In step S1003, the CPU 201 determines whether any region name or disease name is detected from the medical image which the doctor currently interprets. If the CPU 201 determines that a region name or disease name is detected from the medical image which the doctor currently interprets, the process advances to processing in a priority level setting unit 902. This allows the priority level setting unit 902 to sequentially recognize region names or disease names detected from the medical image, of a plurality of medical images, which the doctor currently interprets.

If the CPU 201 determines that no region name or disease name is detected from the medical image which the doctor currently interprets, the process advances to step S1004. In step S1004, the CPU 201 determines whether the doctor has interpreted all the medical images. If the CPU 201 determines that the doctor has not interpreted all the medical images, the process returns to step S1002. If the CPU 201 determines that the doctor has interpreted all the medical images, the CPU 201 terminates the processing in the interpretation state detection unit 901.

<3. Function of Priority Level Setting Unit 902>

Figure 11:
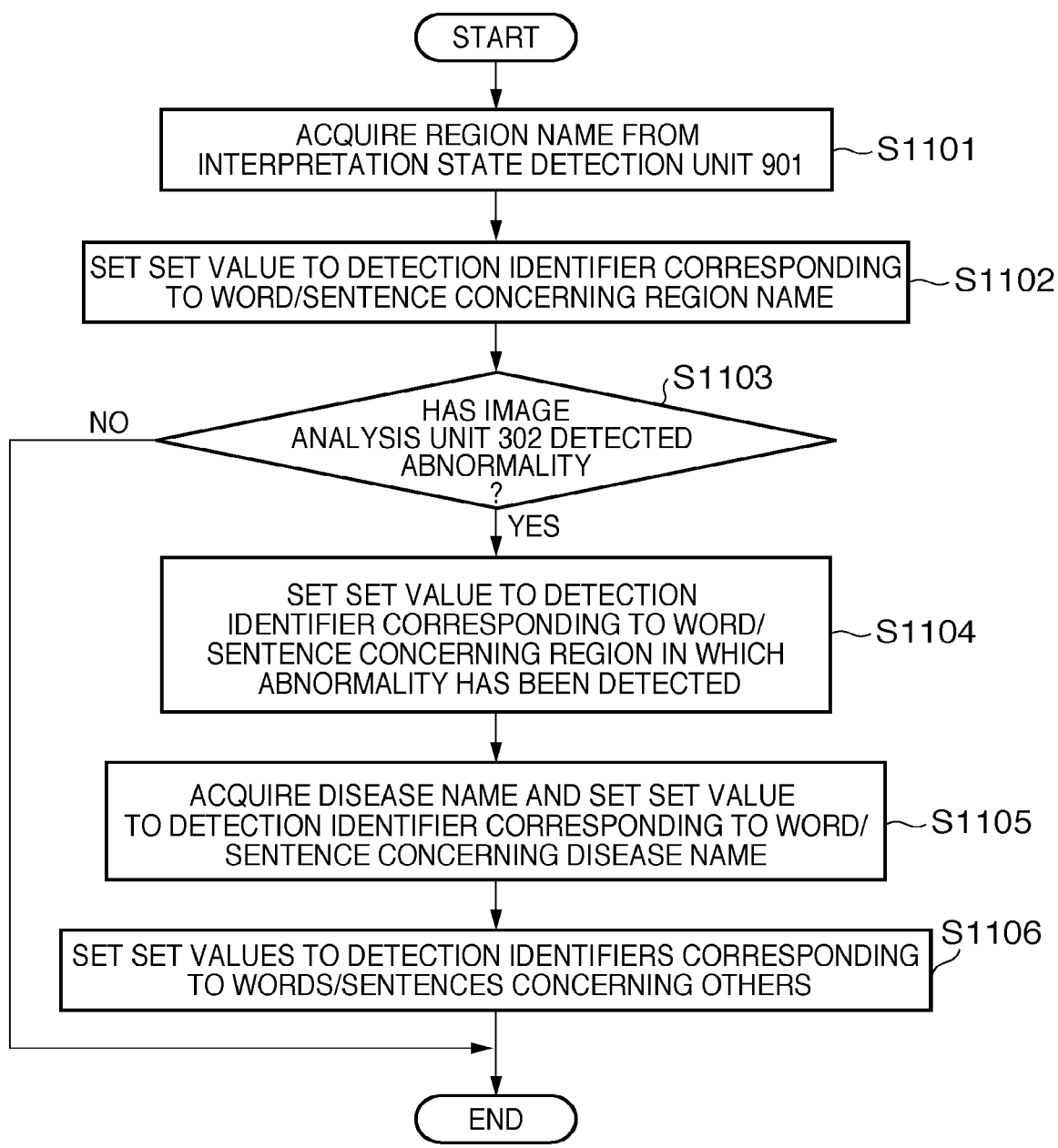
FIG. 11 is a flowchart showing the contents of processing in a priority level setting unit.

The contents of processing in the priority level setting unit 902 will be described next with reference to FIG. 12 along the flowchart of FIG. 11. FIG. 11 is a flowchart showing a processing procedure in the priority level setting unit 902. FIG. 12 is a view showing an example of a conversion candidate table in a state in which the doctor has completed interpretation on the medical image data of a chest portion when the medical image data includes the organ area from the chest portion to the abdominal portion, and the image analysis unit 302 has detected abnormalities in the chest portion and the abdominal portion.

In step S1101, the CPU 201 acquires the region name acquired by the interpretation state detection unit 901.

In step S1102, the CPU 201 searches the conversion candidate table 209 and sets a predetermined set value in "detection identifier" 401 associated with a word/sentence (a word/sentence corresponding to "region" in "type" 402) concerning the region name acquired in step S1101.

More specifically, as shown in FIG. 12, the CPU 201 sets "0101" to a detection identifier associated with a word/sentence which is included in the input medical image data and concerns a region name which the doctor has not interpreted (see "1201").

In addition, the CPU 201 sets "0001" to a detection identifier associated with a word/sentence which is included in the medical image data and concerns a region name which the doctor has already interpreted (see "1202").

On the other hand, the CPU 201 sets "0000" to a detection identifier associated with a word/sentence concerning a region name which is not included in the input medical image data.

Subsequently, in step S1103, the CPU 201 causes a branch depending on whether the image analysis unit 302 has detected any abnormality. If the image analysis unit 302 has detected no abnormality, the CPU 201 terminates the processing in the priority level setting unit 902.

If the image analysis unit 302 has detected an abnormality, the CPU 201 sets a predetermined set value to a detection identifier associated with a word/sentence concerning the region name of a region in which an abnormality is included (a word/sentence corresponding to "region" in "type" 402) in step S1104.

More specifically, as shown in FIG. 12, the CPU 201 sets "0111" to a detection identifier associated with a word/sentence concerning the region name of a region in which the image analysis unit 302 has detected an abnormality and which the doctor has not interpreted (see "1203").

The CPU 201 also sets "0011" to a detection identifier associated with a word/sentence concerning the region name of a region in which the image analysis unit 302 has detected an abnormality and which the doctor has already interpreted (see "1204").

In addition, in step S1105, the CPU 201 acquires the disease name detected by the image analysis unit 302 in image analysis, and searches a conversion candidate table 209 based on the acquired disease name. The CPU 201 then sets a predetermined set value to a detection identifier associated with a word/sentence concerning the acquired disease name (a word/sentence corresponding to "disease" in "type" 402).

More specifically, the CPU 201 sets a set value in the following manner:

(1) In the case of a word/sentence concerning an acquired disease name (a word/sentence corresponding to "disease" in "type" 402) which is included in the medical image data which the doctor currently interprets:

if the disease name has already been read out, the CPU 201 sets "0001" to a detection identifier associated with a word/sentence concerning the disease name (see "1205"); and if the disease name has not been read out, the CPU 201 sets "0101" to a detection identifier associated with a word/sentence concerning the disease name (see "1206").

(2) In the case of a word/sentence concerning an acquired disease name (a word/sentence corresponding to "disease" in "type" 402) which is not included in the medical image data which the doctor currently interprets:

if the disease name has already been read out, the CPU 201 sets "0011" to a detection identifier associated with a word/sentence concerning the disease name (see "1207"); and if the disease name has not been read out, the CPU 201 sets "0111" to a detection identifier associated with a word/sentence concerning the disease name (see "1208").

(3) In the case of a word/sentence other than those concerning the acquired disease name (a word/sentence corresponding to "disease" in "type" 402):

the CPU 201 sets "0000" to a detection identifier associated with this word/sentence.

Assume that the priority levels of the set values set in "detection identifier" 401 are 0011>0001>0010>0111>0101>0000 in the display control unit 307.

In step S1206, the CPU 201 sets a predetermined set value in "detection identifier" 401 associated with a word/sentence other than those concerning the acquired region name or disease name (a word/sentence corresponding to "degree" or "others" in "type" 402).

A case in which an unclearly demarcated node is detected in a lobus inferior will be described as an example. In this case, the CPU 201 sets "0011" in "detection identifier" 401 associated with a word/sentence other than a region name/disease name, for example, "unclearly demarcated", "recognize", "can see", and "suspect", and also associated with the acquired region name or disease name (see "1209").

<4. Function of Conversion Candidate Prediction Unit 903>

The contents of processing in a conversion candidate prediction unit 903 will be described next. In the conversion candidate prediction unit 903, the CPU 201 searches the conversion candidate table 209 stored in a conversion candidate storage unit 304 and reads out conversion candidates of the character recognized by an input unit 305.

Figure 13:
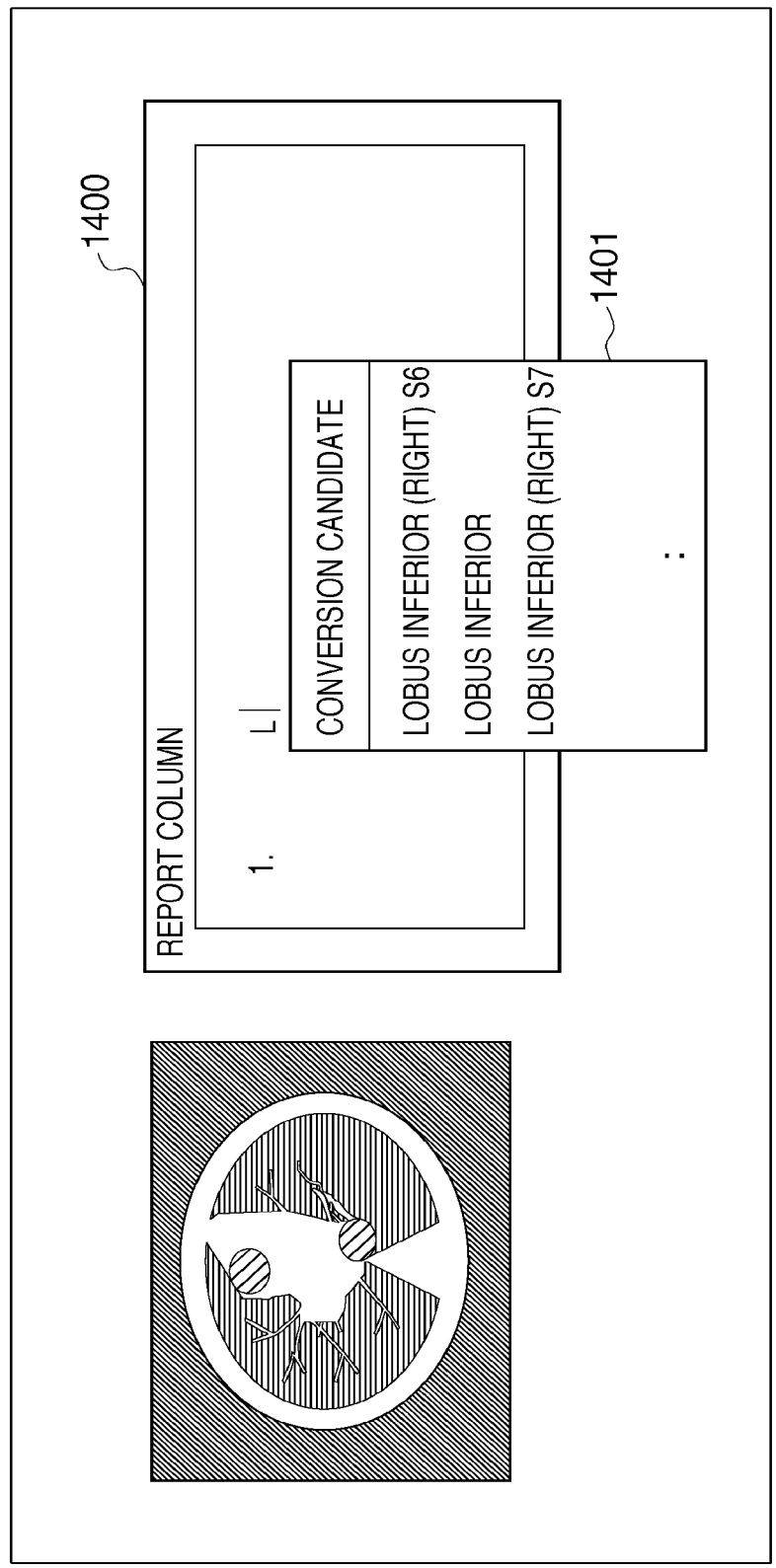
FIG. 13 is a view showing an example of a UI for report creation in the medical image processing apparatus.

A method of reading out conversion candidates will be described below with reference to FIG. 13.

Assume that the doctor has input the character "l" in a report column 1300 displayed on a display device 204 of a medical image processing apparatus 101.

In this case, if conversion candidates of the character (words/sentences starting from "l") are read out from the conversion candidate table 209 in descending order of selection counts as in the prior art, liver, lobus inferior (right) S7, liver artery, lobus inferior (left) S6, lobus inferior (right) S6, and the like are read out in the order named.

In contrast to this, the conversion candidate prediction unit 903 reads out and arranges conversion candidates based on the priority levels of the set values set in "detection identifier" 401 and "selection count" 403 instead of reading out conversion candidates on the basis of the selection counts and the order in which they have currently been read out.

In this case, the priority levels of the set values set in "detection identifier" 401 are 0011>0001>0010>0111>0101>0000. Consequently, lobus inferior (right) S6, lobus inferior, lobus inferior (right) S7, lobus inferior (left) S6, . . . , liver, liver artery, . . . are read out in the order named in the example in FIG. 13. A display unit 308 displays the conversion candidates read out from the conversion candidate table 209 by the display control unit 307.

Although the image analysis unit 302 has detected abnormalities in the chest and abdominal portions, since the doctor has started creating a report before he/she has seen the abnormality in the abdominal portion, words/sentences concerning the chest portion are extracted as conversion candidates of the character "l".

As described above, the medical image processing apparatus according to this embodiment comprises the interpretation state detection unit which detects the interpretation state of the doctor (a medical image which the doctor currently interprets).

With this arrangement, even if a plurality of medical image data is simultaneously input, conversion candidates which are likely to be selected can be displayed in consideration of the medical image which the doctor currently interprets. The doctor can therefore efficiently create a report concerning an interpretation result on the basis of a medical image without any constraints of expression.

Third Embodiment

According to the first and second embodiments described above, the display condition for medical images input by the image input unit and displayed by the display unit remains constant. However, the medical image processing apparatus as the information processing apparatus according to the present invention can display medical image data under various display conditions instead of limiting the number of display conditions for the display of medical images to one. Assume that display conditions are separately set based on the characteristics of each medical imaging apparatus and the set conditions for imaging operation in each hospital.

When medical images are displayed under various display conditions, the region names or disease names to be actually displayed differ depending on display conditions even with respect to the same medical image data.

Figure 14B:
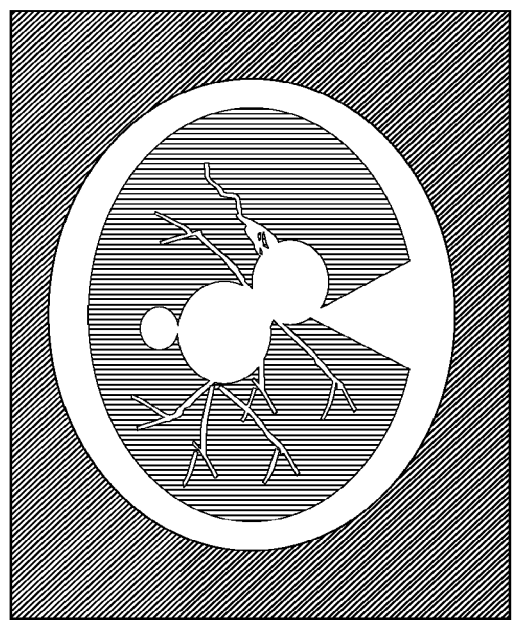
FIGS. 14A and 14B are views each showing an example of a medical image displayed on the medical image processing apparatus.
Figure 14A:
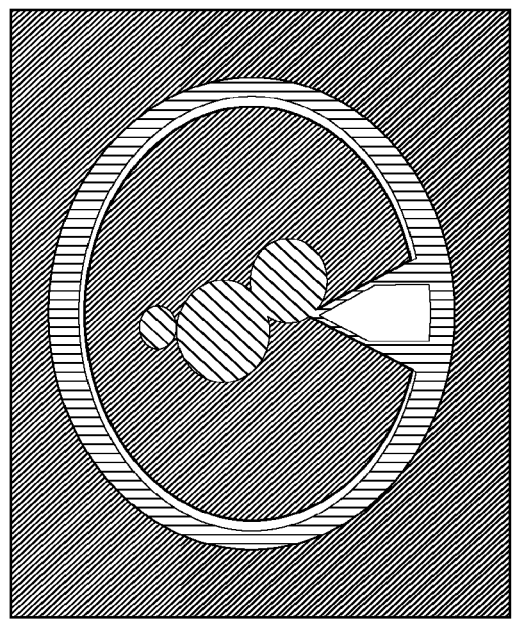

In the case of chest CT data, for example, as shown in FIG. 14A, the lung field is displayed in black under a mediastinum condition which is set to mainly display soft tissues such as a mediastinum and a chest wall.

In contrast, as shown in FIG. 14B, under a lung field condition which is set to mainly display a lung field, a morbid region of the lung field and pulmonary blood vessels are displayed clearly, but all the soft tissues of the mediastinum are displayed in white.

For this reason, in this embodiment, the interpretation state detection unit 901 described above is configured to further manage display conditions at the time of interpretation of medical images. The interpretation state detection unit 901 is also configured to determine a region name or disease name, of the region names or disease names detected from the medical image by image analysis, which can be displayed under an actual display condition, and to increase the priority level of a word/sentence concerning the determined region name or disease name. The contents of processing in the medical image processing apparatus according to this embodiment will be described below.

The contents of processing in an image analysis unit 302, interpretation state detection unit 901, and priority level setting unit 902 in the medical image processing apparatus according to this embodiment are basically the same as those in the second embodiment.

One of 0011, 0001, 0010, 0111, 0101, and 0000 is set in "detection identifier" 401 of a conversion candidate table 209.

In this embodiment, the interpretation state detection unit 901 acquires, as the interpretation state of the doctor, not only a slice No. but also a luminance condition linked with the slice No. In addition, when a medical image is displayed under the luminance condition (display condition), the interpretation state detection unit 901 determines a region name or disease name which can be displayed on the medical image.

The interpretation state detection unit 901 performs this determination every time a medical image is displayed, and specifies a region name or disease name determined as the one that can be displayed on the medical image. In addition, the interpretation state detection unit 901 re-sets a predetermined set value in "detection identifier" 401 associated with a word/sentence concerning the specified region name or disease name.

More specifically, the interpretation state detection unit 901 sets the set value by replacing the most significant digit of the set value which has already been set, that is, "0", with "1" in "detection identifier" 401 associated with a word/sentence concerning the specified region name or disease name.

As a result, one of the set values, that is, 1011, 1001, 1010, 1111, and 1101, is added to "detection identifier" 401 of the conversion candidate table 209.

Assume that the priority levels of the set values set in "detection identifier" 401 are 1011>0011>1001>0001>1010>0010>1111>0111>1101>0101>0000 in a display control unit 307.

As is obvious from the above description, this embodiment can extract region names/disease names which the doctor has actually seen in interpretation, by taking consideration of a display condition as well as a slice No.

Fourth Embodiment

A medical image processing apparatus which learns the description pattern of the doctor and displays conversion candidates on the basis of the learning result will be described next as the fourth embodiment of the present invention.

Figure 15:
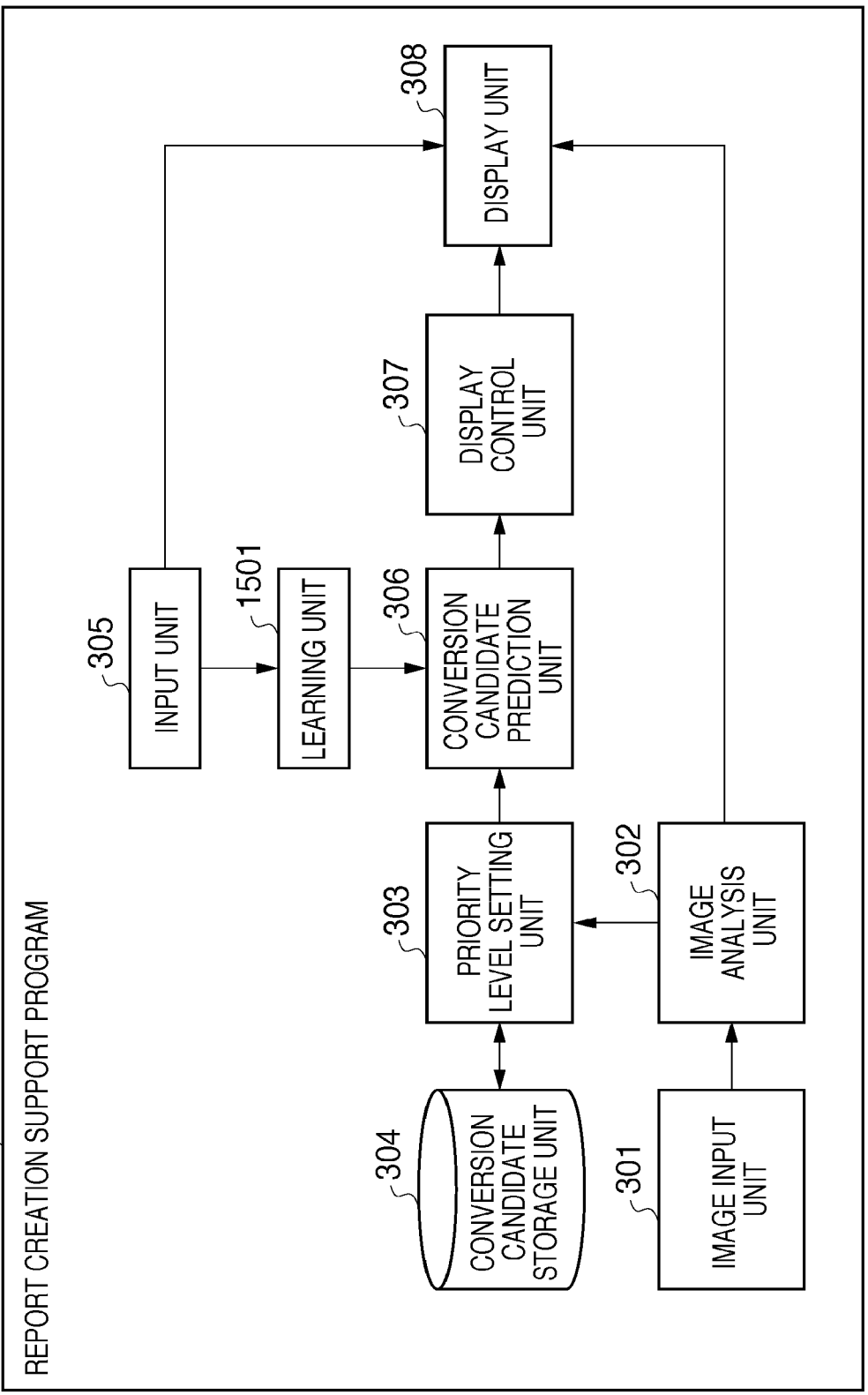
FIG. 15 is a block diagram showing a functional arrangement implemented in a medical image processing apparatus as an information processing apparatus according to the fourth embodiment of the present invention.

FIG. 15 is a block diagram showing the arrangement of the respective functions which a medical image processing apparatus as an information processing apparatus according to the fourth embodiment of the present invention has. As shown in FIG. 15, the basic arrangement of the functions of the medical image processing apparatus according to this embodiment is the same as that of the functions of the medical image processing apparatus according to the first embodiment. However, in addition to the functions which the medical image processing apparatus according to the first embodiment has, the fourth embodiment includes a learning unit 1501 which learns the description pattern of the doctor in report creation.

Including the learning unit 1501, the medical image processing apparatus according to this embodiment can learn a writing style and writing tendencies from an overall syntactic viewpoint when a doctor creates reports.

A writing style includes, for example, the habit of starting writing from a region or a disease. Writing tendencies from an overall syntactic viewpoint include the order of regions in writing an interpretation result.

Note that the learning unit 1501 learns a grammatical rule among words by performing syntactic analysis and semantic analysis on sentences input by the doctor. The apparatus then reads out conversion candidates by using detection identifiers set based on a grammatical rule for each doctor and the numbers of times of selection of conversion candidates.

As is obvious from the above description, the medical image processing apparatus according to this embodiment comprises the learning unit which learns an input rule. This makes it possible to accurately extract a conversion candidate which the doctor wants to write. As a consequence, the doctor can efficiently create a report concerning the contents of interpretation based on a medical image without any constraints of expression.

Fifth Embodiment

In the first embodiment described above, the image analysis unit in the medical image processing apparatus analyzes input medical image data. However, the present invention is not limited to this. For example, the image analysis unit may be implemented by an external device, and the medical image processing apparatus may be configured to receive the image analysis result obtained by the external device.

Figure 16:
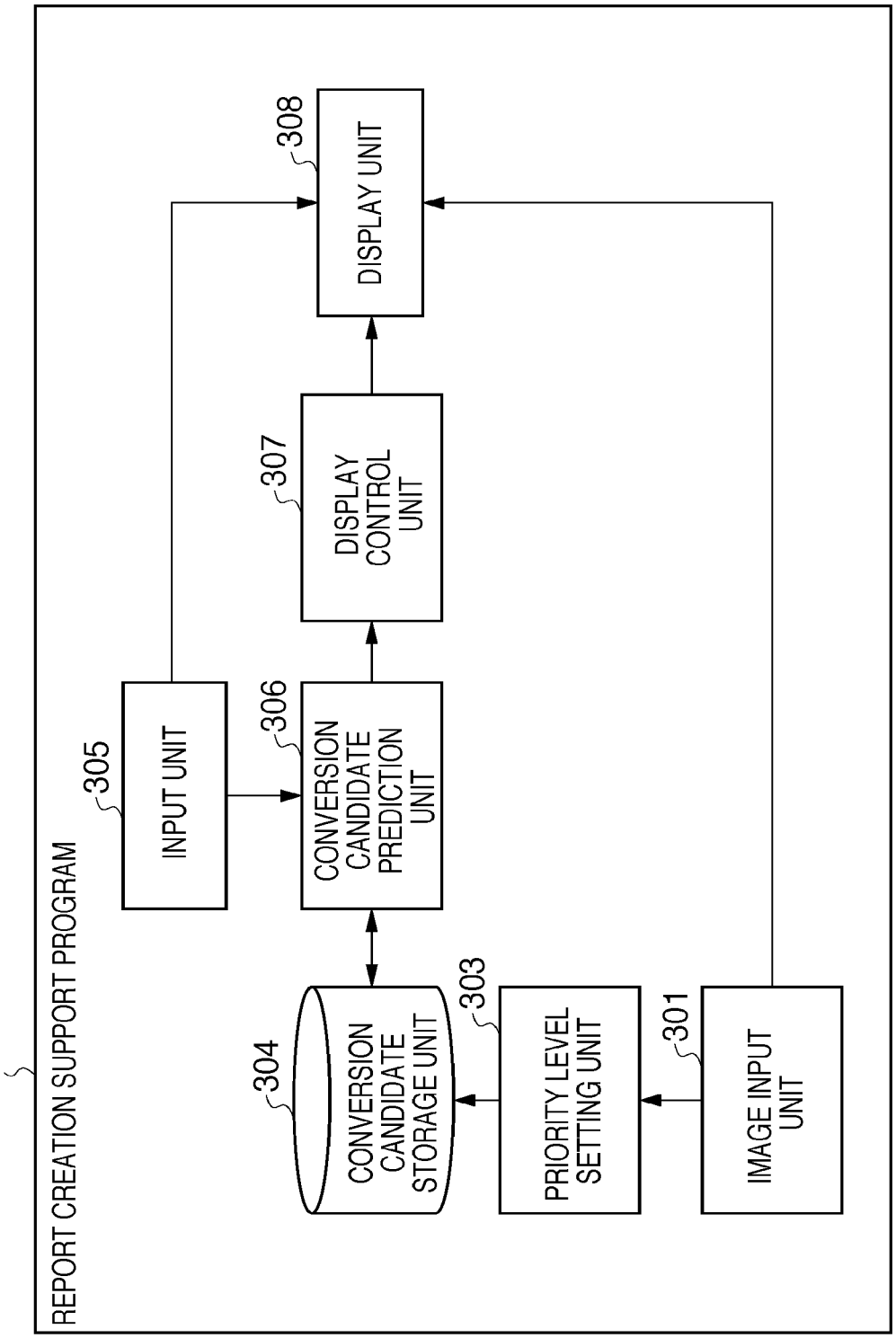
FIG. 16 is a block diagram showing a functional arrangement implemented in a medical image processing apparatus as an information processing apparatus according to the fifth embodiment of the present invention.

FIG. 16 is a block diagram showing a functional arrangement implemented by a medical image processing apparatus as an information processing apparatus according to the fifth embodiment of the present invention. The functions implemented in the medical image processing apparatus according to this embodiment include an image analysis input unit 1601 which inputs the image analysis result transmitted from the external device which analyzes the medical image acquired by a medical imaging apparatus.

The image analysis result transmitted from the external device which analyzes medical images includes medical image data and at least one of a region name, a disease name, the degree of the disease, and the stage of development of the disease included in the medical image data.

Note that the image analysis input unit 1601 can be configured to input the image analysis result obtained outside the medical image processing apparatus by using a network, or can be configured to read out and input an image analysis result stored in a storage medium connected to the medical image processing apparatus.

Figure 17:
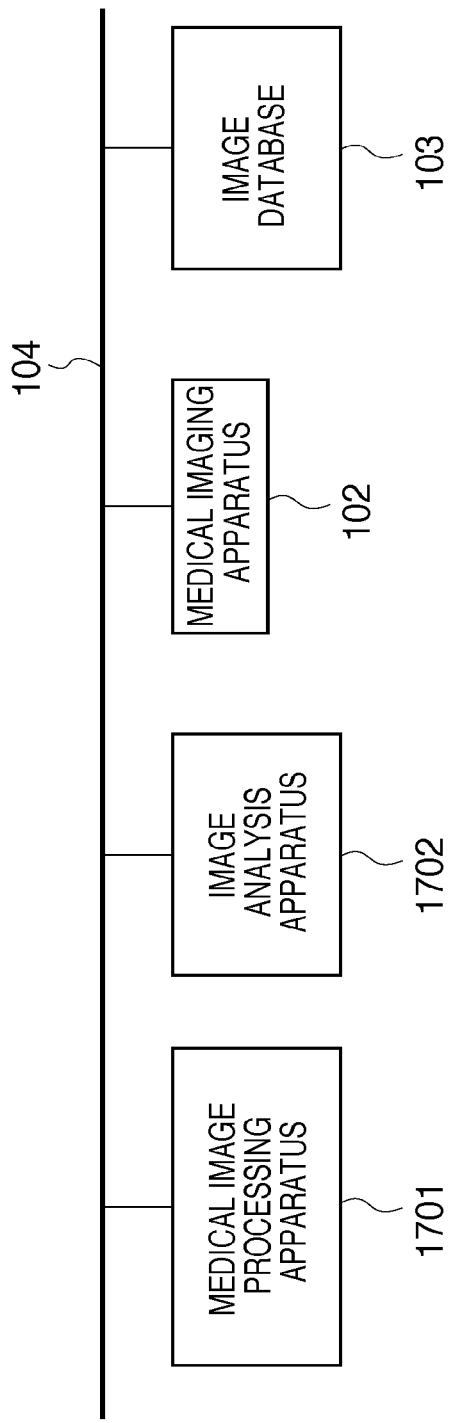
FIG. 17 is a block diagram showing the arrangement of a medical image processing system including the medical image processing apparatus as the information processing apparatus according to the fifth embodiment of the present invention.

FIG. 17 is a block diagram showing how a medical image processing apparatus 101 and an external device 1701 are connected via a network.

The medical image processing apparatus 101 displays conversion candidates by using the image analysis result transmitted from the external device 1701. This makes it possible to display conversion candidates which are likely to be selected, even if the medical image processing apparatus does not include an image analysis unit. The doctor can therefore efficiently create a report concerning the contents of interpretation based on a medical image without any constraints of expression.

Sixth Embodiment

The first to fifth embodiments each have exemplified the case in which words/sentences concerning the character input by the doctor are displayed in a pull-down menu form in report creation. However, the present invention is not limited to this.

As shown in FIG. 18, for example, conversion candidates which are likely to be selected may be sequentially displayed in a list in a standardized form based on an image analysis result.

Other Embodiments

The present invention may be applied to a system constituted by a plurality of devices (e.g., a host computer, an interface device, a reader, a printer, and the like) or an apparatus comprising a single device (e.g., a copying machine, a facsimile apparatus, or the like).

The object of the present invention is implemented even by supplying a storage medium storing software program codes for implementing the functions of the above embodiments to a system or apparatus. In this case, the above functions are implemented by causing the computer (or a CPU or an MPU) of the system or apparatus to read out and execute the program codes stored in the storage medium. In this case, the storage medium storing the program codes constitutes the present invention.

As a storage medium for supplying the program codes, a floppy (registered trademark) disk, a hard disk, an optical disk, a magnetooptical disk, a CD-ROM, a CD-R, a magnetic tape, a nonvolatile memory card, a ROM, or the like can be used.

As is obvious, the functions of the above embodiments are implemented not only when the readout program codes are executed by the computer but also when the OS (Operating System) running on the computer performs part or all of actual processing based on the instructions of the program codes.

The functions of the above embodiments are also implemented when the program codes read out from the storage medium are written in the memory of a function expansion board inserted into the computer or a function expansion unit connected to the computer, and the CPU of the function expansion board or function expansion unit performs part or all of actual processing based on the instructions of the program codes.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. An information processing apparatus, which is communicably connected to a database, for creating a report concerning an interpretation result on a medical image, the information processing apparatus comprising:
   a processor; and
   a memory storing instructions that, when executed by the processor, cause the information processing apparatus to:
      receive a medical image obtained by imaging an object by using a medical imaging apparatus from the database;
      receive region information found in the received medical image;
      input at least one first character relating to the medical image;
      determine a first text candidate and a second text candidate from a plurality of text candidates in a candidate table, based on the at least one first character, wherein the first text candidate describes a first region, and the second text candidate describes a second region, wherein a character length of the first text candidate and a character length of the second text candidate are longer than a character length of the at least one first character;
      determine an interpretation status for the first region and the second region, wherein the interpretation status does not include information representing whether or not the first text candidate and the second text candidate were selected, and wherein the interpretation status indicates whether the medical image has been interpreted;
      determine, based on the determined interpretation status, a priority level for the first text candidate and the second text candidate, wherein if the first region has already been interpreted and the second region has not yet been interpreted, a priority level for the first text candidate is determined to be higher than a priority level for the second text candidate; and
      visually present, based on the determined priority levels for the first text candidate and the second text candidate, the first text candidate and the second text candidate in this order.

2. The information processing apparatus according to claim 1, wherein the first text candidate and the second text candidate include a plurality of characters for conversion of the at least one first character.

3. The information processing apparatus according to claim 2, wherein the memory stores further instructions that, when executed by the processor, cause the information processing apparatus to set priority levels to preferentially present the plurality of characters as the first text candidate and the second text candidate, which concern a result of an analysis of the medical image.

4. The information processing apparatus according to claim 3, wherein the plurality of characters to be presented as the first text candidate and the second text candidate is at least one of a region name included in the medical image.

5. The information processing apparatus according to claim 3, wherein the information processing apparatus arranges the plurality of characters concerning the at least one first character, and presents the plurality of characters as the first text candidate and the second text candidate on the basis of the set priority levels and a number of times of presentation in the past.

6. The information processing apparatus according to claim 3, wherein the information processing apparatus sets in advance the priority levels for the plurality of characters to be non-preferentially presented as the first text candidate and the second text candidate.

7. The information processing apparatus according to claim 3, wherein the memory stores further instructions that, when executed by the processor, cause the information processing apparatus to recognize the medical image of a plurality of medical images and to recognize a display condition for the medical image, and
   wherein the information processing apparatus sets the priority levels to preferentially present the plurality of characters of the medical image, which are included in the display condition.

8. The information processing apparatus according to claim 1, wherein the medical image comprises a plurality of images, and
   wherein a priority level of a text candidate concerning the region information and a disease name, which is from the plurality of images, is increased.

9. The information processing apparatus according to claim 1, wherein each of the first text candidate, and the second text candidate includes a word and a phrase.

10. A method for creating a report concerning an interpretation result on a medical image, the method comprising:
   receiving a medical image obtained by imaging an object by using a medical imaging apparatus from a database;
   receiving region information found in the medical image;
   inputting at least one first character relating to the medical image;
   determining a first text candidate and a second text candidate from a plurality of text candidates in a candidate table, based on the at least one first character, wherein the first text candidate describes a first region, and the second text candidate describes a second region, wherein a character length of the first text candidate and a character length of the second text candidate are longer than a character length of the at least one first character;

determining an interpretation status for the first region and the second region, wherein the interpretation status does not include information relating where or not the first text candidate and the second text candidate were selected, and wherein the interpretation status indicates whether the medical image has been interpreted;

determining, based on the determined interpretation status, a priority level for the first text candidate and the second text candidate, wherein if the first region has already been interpreted and the second region has not yet been interpreted, a priority level for the first text candidate is determined to be higher than a priority level for the second text candidate; and visually presenting, based on the determined priority levels for the first text candidate and the second text candidate, the first text candidate and the second text candidate in this order.

11. The method according to claim 10, wherein the first text candidate and the second text candidate include a first plurality of characters for conversion of the at least one first character.

12. The method according to claim 11, further comprising setting priority levels to preferentially present the first plurality of characters as the first text candidate and the second text candidate, which concern a result of an analysis of the medical image.

13. A non-transitory computer-readable storage medium storing a program which executes a method for creating a report concerning an interpretation result on a medical image, the method comprising:

receiving a medical image obtained by imaging an object by using a medical imaging apparatus from a database;

receiving region information found in the medical image;

inputting at least one first character relating to the medical image;

determine a first text candidate and a second text candidate from a plurality of text candidates in a candidate table, based on the at least one first character, wherein the first text candidate describes a first region, and the second text candidate describes a second region, wherein a character length of the first text candidate and a character length of the second text candidate are longer than a character length of the at least one first character;

determining an interpretation status for the first region and the second region, wherein the interpretation status does not include information relating where or not the first text candidate and the second text candidate were selected, and wherein the interpretation status indicates whether the medical image has been interpreted;

determining, based on the determined interpretation status, a priority level for the first text candidate and the second text candidate, wherein if the first region has already been interpreted and the second region has not yet been interpreted, a priority level for the first text candidate is determined to be higher than a priority level for the second text candidate; and visually presenting, based on the determined priority levels for the first text candidate and the second text candidate, the first text candidate and the second text candidate in this order.

\* \* \* \* \*